United States Patent [19]

Lubisch et al.

[11] Patent Number: 5,270,325
[45] Date of Patent: Dec. 14, 1993

[54] P-HYDROXY PHENONE DERIVATIVES USED IN THE TREATMENT OF CARDIAC ARRHYTHMIA

[75] Inventors: Wilfried Lubisch, Mannheim; Gerda von Philipsborn, Weinheim, both of Fed. Rep. of Germany

[73] Assignee: BASF Aktiengesellschaft, Ludwigshafen, Fed. Rep. of Germany

[21] Appl. No.: 47,570

[22] Filed: Apr. 19, 1993

Related U.S. Application Data

[60] Continuation of Ser. No. 574,119, Aug. 29, 1990, abandoned, which is a division of Ser. No. 379,357, Jul. 13, 1989, Pat. No. 4,980,361.

[30] Foreign Application Priority Data

Jul. 28, 1988 [DE] Fed. Rep. of Germany ........ 3825561

[51] Int. Cl.$^5$ ................. A61K 31/40; A61K 31/445; A61K 31/135
[52] U.S. Cl. .................................. 514/317; 514/428; 514/654
[58] Field of Search ................ 514/317, 428, 654

[56] References Cited

U.S. PATENT DOCUMENTS

| | | | |
|---|---|---|---|
| 4,536,500 | 8/1985 | Bourgery et al. | 514/317 |
| 5,118,682 | 6/1992 | Lubisch et al. | 514/317 |

FOREIGN PATENT DOCUMENTS

| | | |
|---|---|---|
| 164700 | 6/1953 | Australia . |
| 3711677 | 8/1962 | Japan . |

Primary Examiner—Robert W. Ramsuer
Attorney, Agent, or Firm—Oblon, Spivak, McClelland, Maier & Neustadt

[57] ABSTRACT p-hydroxy phenone derivatives of the formula I

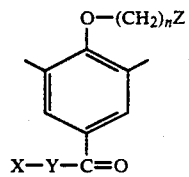

where X is

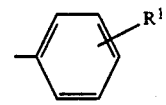

where $R^1$ = F, Cl, Br or trifluoromethyl or a heteroaryl of the structure

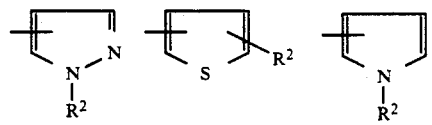

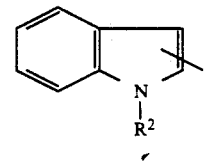

with
$R^2 = C_1-C_4$-alkyl,
Y is a bridging member of the formula —CH=CH—, —CH$_2$CH$_2$— or —CH$_2$—,
n is one of the numbers 2, 3 or 4 and
Z is an amino group of the formula —NR$^2$R$^3$ or N-pyrrolidyl or N-piperidyl, where R$^2$ and R$^3$ are, independently of one another, C$_1$-C$_4$-alkyl, as well as the physiologically tolerated salts thereof, are used for preparing drugs.

3 Claims, No Drawings

P-HYDROXY PHENONE DERIVATIVES USED IN THE TREATMENT OF CARDIAC ARRHYTHMIA

This application is a continuation of application Ser. No. 07/574,119, filed on Aug. 29, 1990, now abandoned, which is a divisional of Ser. No. 07/379,357, filed Jul. 13, 1989, now U.S. Pat. No. 4,980,361.

The present invention relates to p-hydroxy phenone derivatives, to drugs containing them, and to the use thereof for the preparation of antiarrhythmics of Vaughan-Williams class III.

Antiarrhythmics can be classified according to Vaughan-Williams into 4 groups, as follows:
 I. sodium antagonists,
 II. adrenergic $\beta$-receptor blockers,
 III. potassium channel inhibitors,
 IV. calcium antagonists.

Antiarrhythmics of class III often exhibit the therapeutic advantage of acting against arrhythmias which are otherwise resistant to therapy, especially reentry arrhythmias. This has been reported both for amiodarone (Circulation 68 (1) (1983), 88–94) and for D-sotalol (Am. Heart J. 109 (1985), 949–958; J. Clin. Pharmacol. 27 (9) (1987), 708).

p-Hydroxy phenones have been reported to have a variety of physiological actions: spasmolytics (DE 2,616,484, DE 1,174,311, Arch. Pharm. 1966, 299), anti-ulcer agents (JP-A2 52/078-858, JP-A2 52/078-856, JP-A2 51/100-050), amebicides (FR 5003 M); vaso-dilators (JP-B4 27177/65, GB 1,022,648, U.S. Pat. No. 3,407,233, DE 2,062,129, JP-B4 40/06903, JP-B4 40/06904, JP-B4 74/021125); Ca antagonists (EP 201,400; EP 209,435).

By contrast, the p-hydroxy phenone derivatives claimed in the present invention represent, surprisingly, antiarrhythmics of class III.

The present invention relates to p-hydroxy phenone derivatives of the formula I

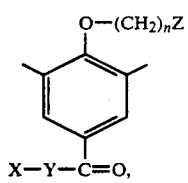

where X is

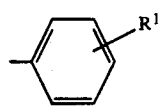

where $R^1$=F, Cl, Br or trifluoromethyl or a heteroaryl of the structure

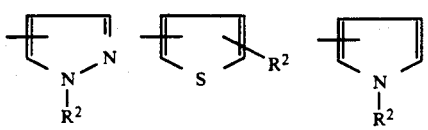

-continued

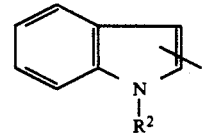

with
$R^2 = C_1-C_4$-alkyl,
Y is a bridging member of the formula —CH=CH—, —CH$_2$CH$_2$— or —CH$_2$—,
n is one of the numbers 2, 3 or 4 and
z is an amino group of the formula —NR$^2$R$^3$ or N-pyrrolidyl or N-piperidyl, where $R^2$ and $R^3$ are, independently of one another, $C_1-C_4$-alkyl, as well as the physiologically tolerated salts thereof.

The compounds according to the invention can be prepared, for example, as shown the following reaction schemes A and B:

Reaction scheme A:

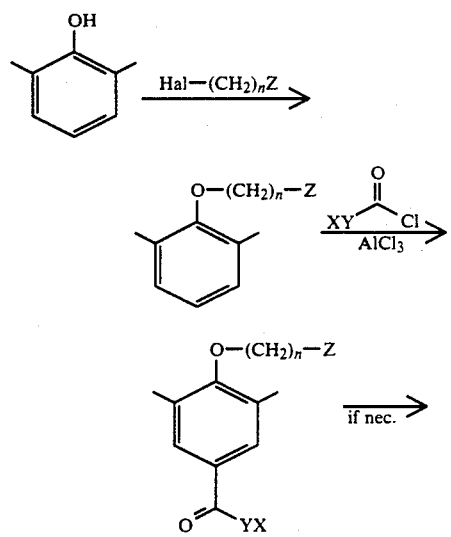

2,6-Dimethylphenol is alkylated in a conventional manner with a haloalkylamine, after which a Friedel-Crafts reaction with an acid chloride X-Y-COCl results in the hydroxy phenone. If Y is the group —CH=CH—, catalytic hydrogenation under conventional conditions results in the propiophenones.

Reaction scheme B:

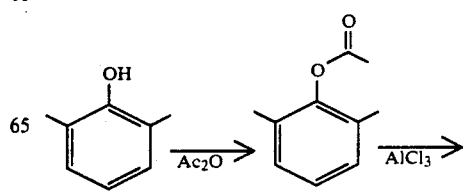

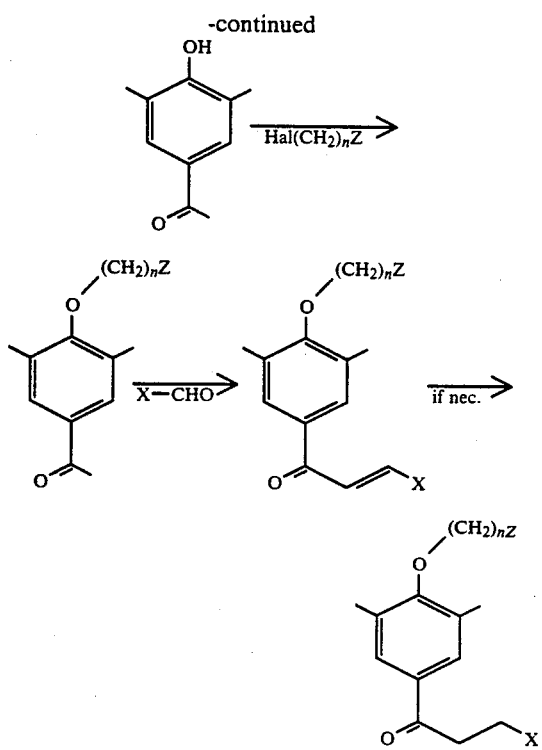

2,6-Dimethylphenol is esterified with acetic anhydride in a conventional manner. The phenol acylation is effected by Fries rearrangement in an AlCl$_3$ melt. The condensation with an aldehyde X-CHO is carried out under basic conditions, conventionally with NaOH. The last two reaction steps can also be carried out in the reverse sequence. Subsequent hydrogenation similar to scheme A results in the propiophenone.

If necessary, the propiophenone derivatives obtained in this way are converted into the addition salt of a physiologically tolerated acid. A compilation of conventional physiologically tolerated acids can be found in Fortschritte der Arzneimittelforschung (Advances in Drug Research) 1966, Birkhäuser Verlag, vol. 10, pages 244 to 285, Germany, Switzerland.

As a rule, the acid addition salts are obtained in a conventional manner by mixing the free base or solutions thereof with the appropriate acid or solutions thereof in an organic solvent, for example a lower alcohol such as methanol, ethanol or propanol, or a lower ketone such as acetone, methyl ethyl ketone or methyl isobutyl ketone, or an ether such as diethyl ether, tetrahydrofuran or dioxane. Mixtures of the said solvents can be used to improve crystallization. In addition, pharmaceutically acceptable aqueous solutions of acid addition compounds of the p-hydroxy phenone derivatives of the formula I can be prepared by dissolving the free bases in an aqueous solution of the acid.

The present invention also relates to therapeutic agents for topical and, especially, systemic administration, which contain a compound of the formula I, besides conventional carriers and/or other pharmaceutical aids, as active substance, and to the use of a compound of the formula I for the preparation of a drug, in particular of an antiarrhythmic.

The novel compounds have, as is shown by the following experimental results, a good class III antiarrhythmic action:

The experimental animals are male and female Pirbright white guinea-pigs weighing from 300 to 500 g. They are anesthetized with 1.5 g/kg urethane i.p. The substances are administered intravenously. The ECG conduction times and the heart rate are measured from a recording from extremity lead II. The measured variables are the QT and PQ intervals and the heart rate. 4 to 6 animals are used per dose. The criterion of a class III action is an increase in the QT interval compared with the values before administration of the substance. An increase in PQ and a large decrease in the heart rate serve as exclusion criteria. The ED 20% is calculated from the linear relation between log dose (mg/kg) of the substance and the relative increase in the QT interval (in %).

TABLE 1

| Class III antiarrhythmic action in guinea-pigs after intravenous administration. ||
|---|---|
| Example | Increase in the QT interval ED 20% [mg/kg] |
| 2 | 1.1 |
| 4 | 1.2 |
| 5 | 1.0 |
| D-Sotalol | 3.6 |

The novel substances are therefore suitable for the treatment of arrhythmias otherwise resistant to therapy, in particular they eliminate ventricular tachycardias occurring after myocardial infarct and based on a reentry mechanism (Lit. Cardiac Arryythmia, Ed. P. Brugada, H. J. J. Wellens, Futura Publishing Co., Mount Kisko, New York 1987).

The therapeutic agents or compositions are prepared by mixing the active substance with the conventional liquid or solid carriers or diluents and the aids conventionally used in pharmaceutical technology, in accordance with the desired mode of administration and with the dosage suitable for the application.

The agents can be administered orally, parenterally or topically. Examples of compositions of this nature are tablets, film-coated tablets, sugar-coated tablets, capsules, pills, powders, solutions or suspensions, infusion or injection solutions as well as pastes, ointments, gels, creams, lotions, dusting powders, solutions or emulsions and sprays.

The therapeutic agents can contain the compounds to be used according to the invention in a concentration of from 0.0001 to 1%, preferably 0.001 to 0.1%, for local application and preferably in a single dose of from 10 to 500 mg for systemic administration and can be administered in one or more doses each day, depending on the nature and severity of the disease.

Examples of aids conventionally used in pharmaceutical technology are, for local application, alcohols such as ethanol, isopropanol, ethoxylated castor oil or ethoxylated hydrogenated castor oil, polyacrylic acid, glycerol monostearate, liquid paraffin, petrolatum, lanolin, polyethylene glycol, polypropylene glycol, stearate and ethoxylated fatty alcohol and, for systemic administration, lactose, propylene glycol and ethanol, starch, talc and polyvinylpyrrolidone. It is also possible to add to the products an antioxidant, for example tocopherol and butylated hydroxyanisole or butylated hydroxytoluene, or additives to improve the flavor, stabilizers, emulsifiers, bleaching agents etc. It is requisite that all the substances used in the preparation of pharmaceutical compositions are toxicologically innocuous and compatible with the active substances used.

EXAMPLE 1

4-Chloro-3',5'-dimethyl-4'-[2-(N-pyrrolidinyl)ethoxy]-chalcone semifumarate 46.7 g (0.38 mole) of 2,6-dimethylphenol, 65.0 g (0.38 mole) of N-(2-chloroethyl)pyrrolidine hydrochloride, 210.1 g (1.52 mole) of potassium carbonate and 2 g of NaI in 300 ml of ethyl methyl ketone were refluxed for 48 h. The reaction mixture was concentrated under reduced pressure, the residue was partitioned between water and ether, the organic phase was separated off, washed with water and dried, and excess ethereal hydrogen chloride solution was added. The precipitated product was recrystallized from 10/1 ethyl acetate/isopropanol. 63 g of N-[2-(2,6-dimethylphenoxy)ethyl]pyrrolidine hydrochloride were obtained.

To 10.0 g (40 mmole) of the above product dissolved in 50 ml of methylene chloride were added 10.1 g (50 mmol) of E-4-chlorocinnamoyl chloride dissolved in methylene chloride, and subsequent 10.7 g (80 mmole) of anhydrous aluminum chloride in portions. The reaction mixture was refluxed for 1 h and then poured into ice/hydrochloric acid, the mixture was made alkaline with dilute sodium hydroxide solution, and the organic phase was separated off, washed with water, dried and concentrated under reduced pressure. The residue was dissolved in hot i-propanol, and an equimolar amount of fumaric acid dissolved in boiling i-propanol was added. The mixture was concentrated and the residue was recrystallized from ethanol/H$_2$O.

4.9 g of the product were obtained. Melting 215°-217° C.

EXAMPLE 2

3,5-Dimethyl-4-[2-(1-pyrrolidinyl)ethoxy]phenyl E-2-(1-methyl-2-pyrrolyl)ethenyl ketone fumarate 100 g (0.82 mole) of 2,6-dimethylphenol and 167.4 g (1.64 mole) of acetic anhydride were refluxed for 4 h. The reaction mixture was poured onto ice and extracted with methylene chloride. The organic phase was washed with dilute sodium hydroxide solution, dried and concentrated under reduced pressure. 138 g of 2,6-dimethylphenyl acetate were obtained. To this product were added 120.2 g (0.9 mole) of anhydrous aluminum chloride in portions, during which the temperature rose to 85° C. The mixture was then heated at 110° C. for 30 min and left to cool. The viscous paste was poured onto ice/hydrochloric acid, and the precipitated product was filtered off. Recrystallization from 1/1 methanol/water resulted in 103.6 g of 3,5-dimethyl-4-hydroxyacetophenone.

39.8 g (0.24 mole) of the above product, 32.6 g of N-(2-chloroethyl)pyrrolidine, 66.3 g (0.48 mole) of potassium carbonate and 0.5 g of cryptand-[2.2.2] in 300 ml of acetonitrile were refluxed for 2 h. The carbonate was filtered off, and the filtrate was concentrated under reduced pressure. The residue was partitioned between methylene chloride and dilute sodium hydroxide solution, and the organic phase was washed with water, dried and concentrated under reduced pressure. 40.5 g of 3-5-dimethyl-4-(2-(1-pyrrolidinyl)ethoxy)acetophenone were obtained as a crude product which was immediately processed further.

5.2 g (20 mmol) of the above product and 4.4 g (40 mmol) of 1-methyl-2-pyrrolecarbaldehyde were dissolved in 100 ml of methanol, 8 g of 50% strength sodium hydroxide solution were added, and the mixture was refluxed for 1 h. The reaction mixture was concentrated under reduced pressure, the residue was partitioned between water and methylene chloride, and the organic phase was dried and concentrated under reduced pressure. The residue was taken up a little hot isopropanol, and an equimolar amount of fumaric acid dissolved in isopropanol was added. The solution was left to crystallize, resulting in 7.5 g of the target product. Melting point 198°-201° C.

The following were prepared in a similar manner to Example 2

3. 3,5-Dimethyl-4-[2-(1-pyrrolidinyl)ethoxy]phenyl E-2-[1-(i-propyl)-4-pyrazolyl]ethenyl ketone dihydrochloride.

4. 3,5-Dimethyl-4-[2-(1-pyrrolidinyl)ethoxy]phenyl E-2-(3-methyl-2-thienyl)ethenyl ketone fumarate Melting point 167°-169° C.

5. 3',5'-Dimethyl-4'-[2-(1-pyrrolidinyl)ethoxy]-2-trifluoromethylchalcone fumarate. Melting point 171°-174° C.

6. 2-Chloro-3',5'-dimethyl-4'-[2-(1-pyrrolidinyl)ethoxy]chalcone hydrochloride. Melting point 181°-184° C.

7. 3,5-Dimethyl-4-[2-(1-pyrrolidinyl)ethoxy]phenyl E-2-(1-indolyl)ethenyl ketone fumarate. Melting point 217°-219° C.

The following was prepared from the compound of Example 5 by hydrogenation similar to Example 1:

8. 3,5-Dimethyl-4-[2-(1-pyrrolidinyl)ethoxy]-3'-(2-trifluoromethylphenyl)propiophenone fumarate Melting point 151° C.

We claim:

1. A method of treating cardiac arrhythmia of the Vaughan-Williams Type III, comprising;
   administering to a subject suffering from arrhythmia a therapeutically effective amount of a composition containing a p-hydroxyphenone compound of formula I:

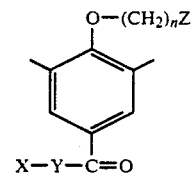

wherein X is

wherein R$^1$=F, Cl, Br or trifluoromethyl,
Y is a bridging member of the formula —CH=CH—, —CH$_2$CH$_2$— or —CH$_2$—,
n is one of the numbers 2, 3 or 4 and
Z is an amino group of the formula —NR$^2$R$^3$ or N-pyrrolidyl or N-piperidyl, where R$^2$ and R$^3$ are, independently of one another, C$_1$-C$_4$-alkyl, as well as the physiologically tolerated salts thereof,
in combination with pharmaceutically acceptable excipients.

2. The method of claim 1, wherein the concentration of active p-hydroxyphenone compound in the composition ranges from 0.0001 to 1%.

3. The method of claim 1, wherein said subject is administered from 10 to 500 mg of said p-hydroxyphenone compound per single dose.

* * * * *